US006736639B1

United States Patent
Summer

(10) Patent No.: US 6,736,639 B1
(45) Date of Patent: May 18, 2004

(54) DENTAL INSERT

(75) Inventor: John D. Summer, Portland, OR (US)

(73) Assignee: Dental Innovations LLC, Portland, OR (US)

( * ) Notice: Subject to any disclaimer, the term of this patent is extended or adjusted under 35 U.S.C. 154(b) by 0 days.

(21) Appl. No.: 09/882,419

(22) Filed: Jun. 15, 2001

Related U.S. Application Data

(60) Provisional application No. 60/216,196, filed on Jul. 6, 2000.

(51) Int. Cl.$^7$ .................................................. A61C 5/04
(52) U.S. Cl. .......................................................... 433/39
(58) Field of Search ................................. 433/149, 148, 433/39, 40, 155, 226

(56) References Cited

U.S. PATENT DOCUMENTS

| | | |
|---|---|---|
| 638,973 A | 12/1899 | Mehlig |
| 804,099 A | 11/1905 | Chase |
| 1,133,379 A | 3/1915 | Hollingsworth |
| 1,265,581 A | 5/1918 | Zurbrigg |
| 1,669,231 A * | 5/1928 | Curran |
| 1,794,213 A | 2/1931 | Spahn |
| 2,288,011 A | 6/1942 | Mizzy |
| 2,353,747 A | 7/1944 | Morrison |
| 2,538,486 A * | 1/1951 | Tofflemire |
| 2,591,745 A | 4/1952 | Tofflemire |
| 2,607,117 A | 8/1952 | Baughan |
| 2,790,238 A | 4/1957 | Trangmar |
| 2,835,628 A | 5/1958 | Saffir |
| 3,074,169 A | 1/1963 | Freeman |
| 3,082,531 A | 3/1963 | Jacobsen |
| 3,145,472 A | 8/1964 | Tofflemire |
| 3,305,928 A | 2/1967 | Tofflemire |
| 3,421,222 A | 1/1969 | Newman |
| 3,842,505 A | 10/1974 | Eames |
| 4,024,643 A | 5/1977 | Eisenberg |
| 4,373,915 A | 2/1983 | Comstock |
| 4,523,909 A | 6/1985 | Lazarus ....................... 433/39 |
| 4,563,152 A | 1/1986 | McClure |
| 4,608,021 A | 8/1986 | Barrett ....................... 433/229 |

(List continued on next page.)

FOREIGN PATENT DOCUMENTS

| | | |
|---|---|---|
| EP | 0241 197 A1 | 3/1987 |
| WO | WO 01/43656 A1 | 6/2001 |

OTHER PUBLICATIONS

US 5,591,801, 1/1997, Weissenfluh et al. (withdrawn)
Dental Products, "Matrix Bands" product description, Jul. 1998.
Dental Products Report, Light–Curing Matrix, Nov. 1999.
Summer et al., Method of Making a Tooth Spacer, filed Jul. 6, 2000, application Ser. No. 09/611,110.

(List continued on next page.)

Primary Examiner—Kevin Shaver
Assistant Examiner—Melba Bumgarner
(74) Attorney, Agent, or Firm—Klarquist Sparkman LLP

(57) ABSTRACT

Tooth inserts are described for use in restoring teeth having a proximal surface requiring restoration and an, intact proximal surface not requiring restoration. A tooth insert according to one disclosed embodiment comprises an elongated band having first and second spaced apart central portions. The central portions are positioned so that when the band is wrapped around a first tooth, the first central portion is positioned between the prepared surface of the first tooth and a second adjacent tooth and the second central portion is positioned between the intact surface of the first tooth and a third tooth at the opposite side of the first tooth from the second tooth. An aperture is formed in the second central portion to permit at least partial interproximal contact between the first and third tooth through the aperture to minimize separation between the first and third teeth caused by the thickness of the band.

35 Claims, 2 Drawing Sheets

U.S. PATENT DOCUMENTS

| | | |
|---|---|---|
| 4,704,087 A | 11/1987 | Dragan .......................... 433/39 |
| 4,718,849 A | 1/1988 | von Weissenfluh et al. ... 433/39 |
| 4,909,736 A | 3/1990 | Ritter .......................... 433/39 |
| 5,330,353 A | 7/1994 | Wavrin ......................... 433/39 |
| 5,342,194 A | 8/1994 | Feldman ....................... 433/39 |
| 5,380,198 A | 1/1995 | Suhonen ....................... 433/39 |
| 5,505,618 A | 4/1996 | Summer ..................... 433/148 |
| 5,586,883 A | 12/1996 | Nakisher et al. .............. 433/39 |
| 5,791,898 A | 8/1998 | Maissami ................... 433/164 |
| 5,899,694 A | 5/1999 | Summer ..................... 433/136 |
| 6,142,778 A | 11/2000 | Summer ....................... 433/39 |
| 6,234,793 B1 * | 5/2001 | Brattesani et al. .......... 433/149 |
| 6,350,122 B1 * | 2/2002 | Meyer .......................... 433/39 |

OTHER PUBLICATIONS

Summer et al., Tooth Spacer, filed Jul. 6, 2000, application Ser. No. 09/611,187.

Summer et al., Method and Apparatus for Shaping Dental Filling Material, filed Dec. 16, 1999, application Ser. No. 09/465,413.

*Sullivan–Schein Dental Catalogue,* pp. 313–314 (publication date unknown but published prior to Jul. 5, 1999).

* cited by examiner

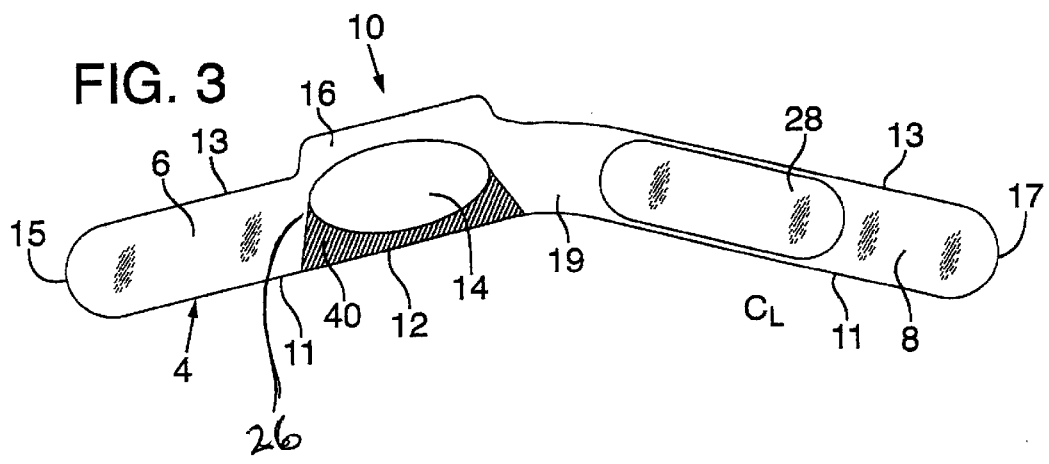
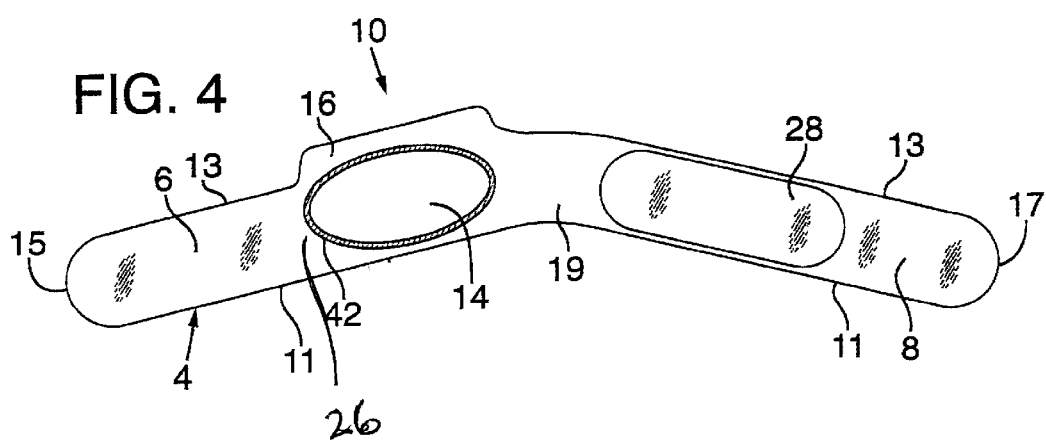
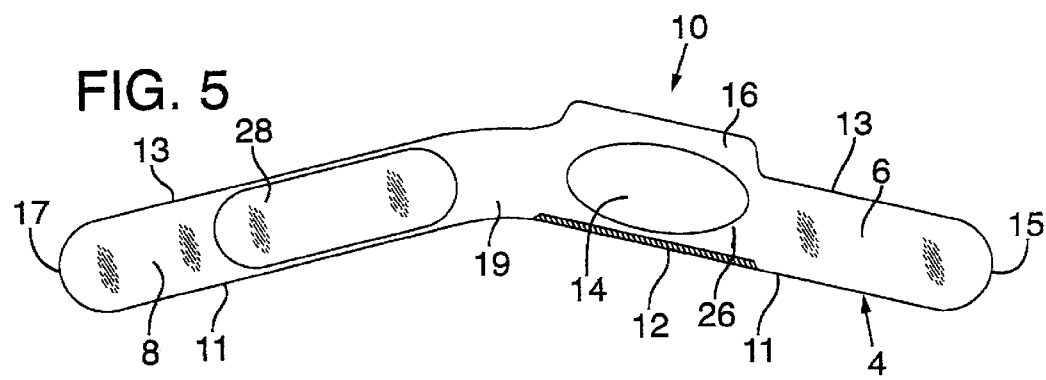

DENTAL INSERT

CROSS REFERENCE TO RELATED APPLICATION

This application claims priority to applicant's provisional application No. 60/216,196, filed Jul. 6, 2000, which is incorporated herein by reference in its entirety.

FIELD

The present invention relates to the field of dental devices and in particular, to tooth inserts for positioning between teeth.

BACKGROUND

In dentistry, teeth which are subject to decay are typically drilled or otherwise prepared by removing the decayed tooth material. This leaves an aperture, slot or other void in the tooth which is then filled with composite resin or other filling material. A class 2 filling is a dental procedure in which a decayed area of a tooth along a portion of one or both proximal surfaces is prepared and filled. The proximal surfaces of a tooth are those surfaces of the tooth that face the surface of an adjacent tooth. The proximal surface that faces an adjacent tooth toward the front of the dental arch may be referred to as the mesial proximal surface. The proximal surface that faces an adjacent tooth toward the back of the dental arch may be referred to as the distal proximal surface.

When dentists perform class 2 cavity preparations, they typically insert a temporary substrate adjacent to the cavity preparation to contain and shape the filling material. The temporary substrate that dentists have traditionally used is an elongated band called a matrix band. Matrix bands are typically formed from a flexible metal strip, such as a stainless steel strip about ¼ inch wide and about 0.001 to 0.002 inch thick. One example of a matrix band is disclosed in U.S. Pat. No. 2,591,744 to Tofflemire.

Before being placed in the patient's mouth, a matrix band usually is placed in a retaining device or other type of tool to position and tighten the band around the tooth so that it at least partially surrounds and conforms closely to the shape of the tooth. Examples of such devices are the Tofflemire retainer disclosed in U.S. Pat. No. 2,538,486 to Tofflemire and a windable cylindrical coil disclosed in U.S. Pat. No. 4,523,909 to Lazarus.

When restoring a tooth, it is important to achieve a closed contact between the restored surface and the adjacent tooth to prevent food from becoming impacted between the teeth and causing periodontal disease. One problem with conventional matrix bands is that when they are removed from a class 2 filling made with composite filling material, a gap often remains between the filled tooth and the adjacent tooth. The gap is typically roughly as wide as the thickness of the matrix band which was used in the filling.

To solve the problem of open contacts in class 2 composite fillings, dentists sometimes employ special techniques and tools to wedge apart or otherwise force apart the adjacent teeth during the filling process. After the filling material is cured, the device separating the adjacent teeth is removed to permit the teeth to spring back together, hopefully just far enough to leave a fully closed contact between the teeth. One specific technique involves the use of mechanical wedges driven in place by finger pressure between adjacent teeth at a location well below the contact area. Another known technique involves forcefully separating the teeth by use of a metal ring (known as a bitine ring) which applies powerful forces inward between the teeth at a location just beneath where they meet.

However, such forceful separation of adjacent teeth may be difficult for the dentist and uncomfortable for the patient. Another disadvantage of using techniques involving forceful separation of adjacent teeth is that the extent to which the teeth will spring back together following the procedure is somewhat unpredictable. Moreover, in a class 2 filling in which a matrix band is positioned around a tooth having a prepared proximal surface (i.e., a proximal surface requiring restoration) and an intact proximal surface (i.e., a proximal surface not requiring restoration), the thickness of the band between the intact proximal surface and an adjacent tooth tends to push, or drive, the tooth being filled toward the tooth adjacent the prepared surface. Consequently, additional force is required to adequately wedge apart the adjacent teeth on the side of the prepared surface for packing the filling material into the cavity.

A recent attempt to solve the problem of open contacts that requires less forceful separation of adjacent teeth is to use matrix bands having areas of reduced thickness for insertion between the proximal surfaces of adjacent teeth. However, if a tooth has only one prepared proximal surface, matrix bands of this type can be difficult to place between the tight intact interproximal contact (i.e., the contact between the intact proximal surface not requiring restoration and an adjacent tooth) because the band is very thin and pliable. Such a band may buckle or tear and may not slide through the intact interproximal contact.

Shorter matrix bands are known which provide a form to enclose the proximal surface requiring restoration but are not long enough to completely encircle the tooth, and therefore do not require insertion between the intact interproximal contact. One popular version of a shorter band is known as a sectional matrix. Another version is a preformed, C-shaped band disclosed in U.S. Pat. No. 4,704,087 to Dragan. However, such short matrix bands are undesirable in that they are difficult to tighten around a tooth and maintain a close contact between the inner surface of the band and the outer contour of the prepared tooth to avoid the formation of a ledge at the gingival edge of the filling.

A need exists for an improved tooth insert for use in restoring a tooth having one proximal surface requiring restoration and one intact proximal surface.

SUMMARY

According to one aspect of the disclosure, a tooth insert is provided for engaging around a first tooth having a prepared proximal surface requiring restoration adjacent to a second tooth and an intact proximal surface adjacent to a third tooth at the opposite side of the first tooth from the second tooth. The tooth insert in one form comprises an elongated band having first and second spaced apart central portions. The central portions are positioned so that when the band is wrapped around the first tooth, the first central portion is positioned between the prepared proximal surface of the first tooth and the second tooth and the second central portion is positioned between the intact proximal surface of the first tooth and the third tooth. An aperture is formed in the second central portion to permit at least partial interproximal contact between the first and third tooth through the aperture to minimize separation between the first and third teeth caused by the thickness of the band.

In a disclosed embodiment, the aperture is dimensioned to be larger than the area occupied by the natural, intact interproximal contact of the first and third teeth to eliminate separation therebetween caused by the thickness of the band when the band is positioned around the first tooth. Consequently, when the band is in place around the first tooth for filling, the band does not cause the first tooth to move toward the second tooth, which is adjacent to the prepared cavity. As a result, additional wedging or separation between the prepared proximal surface and the second tooth is not required to permit packing of filling material into the cavity.

The band may include an edge portion of reduced thickness extending along the gingival edge of the band under the aperture to facilitate insertion of the band between the intact interproximal contact of the first and third teeth. The band also may include a projection extending in the occlusal direction above the aperture. The projection adds rigidity to the portion of the band to be inserted between the intact interproximal contact. The projection also provides a convenient location on which a dentist can apply finger pressure to push the band through the intact interproximal contact area. In addition, the first central portion of the band, which is adjacent the prepared cavity when the band is installed, may have a thickness that is less than the thickness of the band.

The present invention is directed toward new and non-obvious aspects and features of a tooth insert, both alone and in various combinations and sub-combinations with one another. In addition, the invention is directed toward new and non-obvious method acts or steps relating to producing a tooth insert, both alone and in combination with one another. These new and non-obvious aspects, features, acts and/or steps and combinations and sub-combinations thereof are set forth in the claims below.

BRIEF DESCRIPTION OF THE DRAWINGS

FIG. 3 shows a side view of a band similar to FIG. 1 in which an area of reduced thickness extends from the aperture to the gingival edge.

FIG. 4 shows a side view of a band similar to FIG. 1 in which an area of reduced thickness surrounds the aperture.

FIG. 5 shows a side view of a band that is the mirror image of the band of FIG. 1 for use in restoring the distal surfaces of upper teeth and the mesial surfaces of lower teeth.

DETAILED DESCRIPTION

Figure 1:
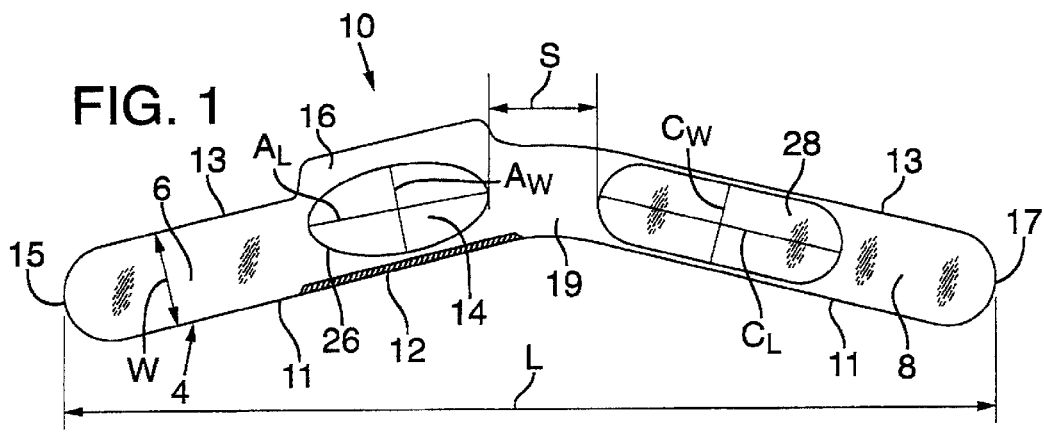
FIG. 1 shows a side view of one embodiment of an elongated band for use in restoring a tooth having an intact proximal surface and a proximal surface prepared for filling.

FIG. 1 shows one embodiment of a tooth insert in the form of an elongated band having a gingival edge 11 and an occlusal edge 13 which is opposed to and spaced from the gingival side 11. The band includes a pair of opposite transversely spaced side edges 15, 17 extending between the respective gingival and occlusal edges 11, 13. The "gingival edge" refers to the edge of the body which is positioned closest to the patients gum when the band is inserted in place. The band 10 comprises an elongated body 4 having first and second elongated leg portions 6, 8 that join together at a central region 19. The body 4 in FIG. 1 is of a somewhat inverted v-shaped configuration with the apex of the configuration being positioned at the central region 19. However, the shape of the body may be varied for different applications or situations. For example, the body may be generally rectangular with parallel gingival and occlusal edges.

Figure 2:
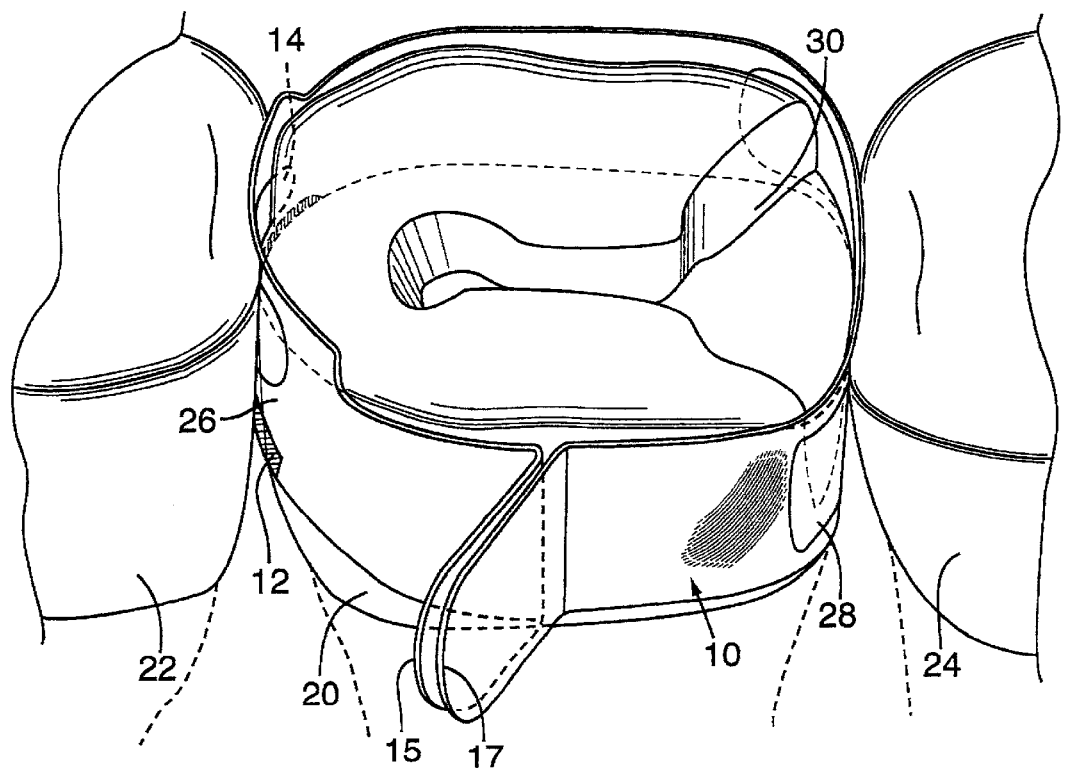
FIG. 2 illustrates the use of a tooth insert of the form shown in FIG. 1.

The body in the form shown has two spaced apart central portions 26, 28, each of which is positioned in a respective one of the elongated leg portions 6, 8. As can be seen in FIG. 2, the central portions are desirably located on the body so that they are positioned at least in part proximal surfaces of adjacent teeth. Thus, with reference to FIG. 2, central portion 26 may be positioned between the adjacent surfaces of teeth 22 and 20 while central portion 28 may be positioned between the adjacent surfaces of teeth 24 and 20. Although not required, central portion 28 desirably may have a thickness that is less than the thickness of the body 4, as explained in greater detail below. In addition, the body is desirably sufficiently elongated to wrap at least partially around a tooth, or more desirably, completely around a tooth, such as shown in FIG. 2.

The body of the dental band 10 may have a monolithic or unitary construction and is desirably, but not necessarily, made of a durable and resilient material such as stainless steel. Alternatively, the body may be made of a multiple piece construction and may be made of materials other than stainless steel.

Although the size of the band may vary, in one specific example, the overall length L of the body of FIG. 1 from side edge 15 to side edge 17 is approximately 2.5 inches. The width of the body shown in FIG. 1, indicated by W, measured along a line perpendicular to the respective edges 11, 13 may be 0.25 inch. The thickness of the body in particular examples ranges from about 0.0015 inch to about 0.003 inch, although the body may be thinner or thicker. A specific example is a thickness of 0.0015 inch. Of course, these specific dimensions (as well as other dimensions provided herein) are given to illustrate the embodiments and not to limit the invention. These dimensions can be modified as needed in different applications or situations.

In FIG. 2, tooth 22 is located on the mesial side of tooth 20, and tooth 24 is located on the distal side of tooth 20. Tooth 20 has a prepared cavity 30 on its distal proximal surface. The mesial proximal surface of tooth 22 is intact and does not require restoration. The adjacent teeth have interproximal contact areas where the teeth are closest to or in contact with one another. Thus, a distal interproximal contact is formed between the distal proximal surface of tooth 20 and the mesial proximal surface of tooth 24. As shown, the cavity preparation has completely eliminated the interproximal contact between tooth 20 and tooth 24. A mesial interproximal contact is formed between the mesial proximal surface of tooth 20 and the distal proximal surface of tooth 22. This also may be referred to as an intact interproximal contact as the mesial proximal surface of tooth 20 does not require restoration.

Leg portion 6 of the illustrated band 10 contains a centrally located aperture 14 positioned in central portion 26 to permit at least partial interproximal contact between the intact proximal surface of tooth 20 and tooth 22 through the aperture and to thereby minimize separation of tooth 20 and tooth 22 that otherwise would be caused by a thickness of the band if positioned between the contact surfaces of teeth 20, 22. Aperture 14 in the illustrated embodiment is oval in shape, with the major axis of the aperture extending generally lengthwise of the band. However, aperture 14 could instead be shaped like a circle, rectangle, a trapezoid, or any of a wide variety of shapes.

Although there is no requirement as to the exact size of aperture 14, desirably, aperture 14 is dimensioned to be larger than the area occupied by the intact interproximal contact, such as larger than the contact area of teeth 20 and 22 in FIG. 2, to maintain the full interproximal contact therebetween and to eliminate separation caused by the thickness of the band when the band is positioned around a tooth. Consequently, when the band is in place around a tooth (e.g., tooth 20) for filling, the band does not cause that tooth to move toward a tooth adjacent to the prepared cavity (e.g., tooth 24 in FIG. 2). As a result, additional wedging or separation between the prepared proximal surface and an adjacent tooth is not required to result in an acceptably tight finished interproximal contact.

As previously mentioned, aperture 14 may be sized to allow the full interproximal contact between the intact proximal surface and the next adjacent tooth, which in this case is tooth 22. However, aperture 14 must not be so large as to overly weaken leg portion 6. Leg portion 6 is desirably rigid enough to withstand the pressure needed to push it down through the intact interproximal contact without tearing or buckling. In a specific example, the length of aperture 14, indicated at $A_L$ in FIG. 1, may be about 0.3 inch and the width of aperture 14, indicated at $A_W$, may be about 0.4 inch, although these dimensions may vary.

Although not required, aperture 14 in the form shown is spaced from the gingival edge 11 and the occlusal edge 13 of leg portion 6 so that a peripheral or reinforcing region of the body bounds aperture 14. Such a construction enhances the rigidity of leg portion 6 to facilitate the insertion of leg 6 down through the intact interproximal without the leg 6 tearing or buckling. The peripheral or reinforcing portions of the body bounding aperture 14 may be varied in thickness, but are generally of the same thickness as the body of the band, which, as mentioned above, may range from about 0.0015 inch to about 0.003 inch. The minimum width of the peripheral or reinforcing portions bounding aperture 14 (i.e., the minimum distance between the periphery of aperture 14 and either the gingival or occlusal edge 11, 13) desirably is at least in a range from about 0.05 to about 0.1 inch and more desirably is at least about 0.06 inch in a specific example. Of course, the above dimensions may be varied and are provided as an example only.

As best shown in FIG. 1, the outline of the body may be extended in the occlusal direction to form a projection, or lip 16, over the aperture 14. Projection 16 may be of any shape which is structurally sound, but in this embodiment is generally rectangular or trapezoidal. Projection 16 adds rigidity to leg portion 6 around aperture 14 and also provides a convenient location on which a dentist can apply finger pressure in order to push the gingival edge 11 of leg portion 6 down through the intact interproximal contact area between teeth 20 and 22.

The central portion 28 of leg portion 8 may have a thickness that is less than the thickness of the body 4 of the band, such as described in U.S. Pat. No. 6,142,778 to Summer, which is incorporated herein in its entirety. Central portion 28 desirably is located within the distal leg portion 8 and is large enough so that, when the matrix band is wrapped around a tooth of almost any size or shape, some portion of the thinned material occupies the area of the interproximal contact. As shown in FIG. 1, thin central portion 28 may be generally oblong with parallel top and bottom edges extending lengthwise of the body and is spaced from the gingival and occlusal edges 11, 13. Alternatively, although less desirable, central portion 28 may extend entirely to the gingival edge 11. Thus, central portion 28 is at least partially surrounded or entirely enclosed by a peripheral or reinforcing region of the body.

As shown, the thin central portion 28 may be larger than aperture 14, because the leg portion 8 does not need to withstand the force of being pushed down through an intact interproximal contact.

Although variable, in a specific example the length of central portion 28, indicated at $C_L$ in FIG. 1, may be about 0.6 inch, and the width of central portion 28, indicated at $C_W$, may be about 0.19 inch. For a stainless steel band having a thickness of about 0.0015 inch, the thickness of central portion 28 may range from about 0.0003 inch to about 0.0006 inch, with a particularly desirable thickness being about 0.0005 inch. The spacing between two vertical lines tangent to the adjacent edges of aperture 14 and central portion 28, indicated by S in FIG. 1, may, for example, be about 0.5 inch. The peripheral or reinforcing portions of the body bounding central portion 28 may be varied in thickness, but are typically the same thickness as the body of the band. The width of the peripheral or reinforcing portions bounding central portion (i.e., the distance between the periphery of central portion 28 and either the gingival or occlusal edge 11, 13) may, for example, range from about 0.03 to about 0.07 inch with a desirable example being about 0.04 inch. The above dimensions may be varied and are provided as specific examples.

In an alternative embodiment, the thickness of central portion 28 is the same as the thickness of the body 4 of the band. In yet another form, central portion 28 may include an opening covered by a sheet of very thin polymer material, such as disclosed in U.S. patent application Ser. No. 09/465,413 entitled "Method and Apparatus for Shaping Dental Filling Material," filed on Dec. 16, 1999, which is incorporated herein in its entirety.

Referring again to FIG. 1, an edge portion 12 having a reduced thickness may be provided to extend along the gingival edge 11 of leg portion 6. In a specific example, edge portion 12 has a thickness of about 0.0005 inch, a length of about 0.75 inch and a width of about 0.5 mm. The gingival edge 11 with thin edge portion 12 facilitates insertion of leg portion 6 down through the intact interproximal contact.

Leg portion 6 may be provided with additional areas of reduced thickness to facilitate insertion and/or removal of the band through the intact interproximal contact area. As shown in FIG. 3, for example, an area 40 of reduced thickness extends from the aperture 14 to the gingival edge 11 to provide a path along which the leg portion 6 can be pushed into place through the intact interproximal contact. In another embodiment, as shown in FIG. 4, an area 42 of reduced thickness is concentric with the aperture 14. Although area 42 is shown to completely surround aperture 14, it may in other examples extend partially around aperture 14, for example, along the lower periphery of the aperture as the band is typically pushed downwardly to insert the band in place and pulled upwardly to remove the band. The width of area 42 in the radial direction may be about 0.5 mm, however, this dimension may vary. For a stainless steel band having a thickness of about 0.0015 inch, the thickness of the areas 40 and 42 shown in FIGS. 3 and 4, respectively, may be from about 0.0004 to about 0.0006 inch with a particularly desirable thickness being about 0.0005 inch.

Although the band 10 is shown in FIG. 2 as being used for filling a portion of a lower tooth that includes the mesial surface, as well as a portion of the occlusal surface (i.e., biting surface) of the tooth, a mirror image of the illustrated band also may be used in the restoration of the distal surface of the same tooth. Both shapes may be provided to dentists together in a kit so that either shape can be selected for a particular restoration.

In addition, the shape of the band 10 can be modified to accomodate different cavity preparations. For example, the body may be extended in the gingival direction under central portion 28 to accommodate cavity preparations which extend in this direction.

The matrix band 10 may be used with commercially available retainer systems, such as the Tofflemire retainer or a windable cylindrical coil. If a windable cylindrical coil is used, the leg portions 6, 8 may be elongated outwardly in the direction of the side edges for use in the coiling mechanism.

The matrix bands described herein may be made by any suitable process. In one approach, a band having an aperture 14 and one or more areas of reduced thickness is formed in a chemical etching process. Previously mentioned U.S. Pat. No. 6,142,778 to Summer describes, in connection with FIGS. 16–18 of the patent, a chemical etching process for forming plural bands from a monolithic sheet of material in which the bands have areas of reduced thickness. Any of the bands described in the present disclosure may be formed in a similar process.

For example, a suitable masking material, such as photo resist, is selectively applied to a sheet of material, such as 0.0015 inch thick stainless steel, in the following manner. First, a first surface of the sheet is masked with spaced apart bands of photo resist, except that areas between the bands and areas within the bands which are to form apertures 14 are desirably left unmasked. The second surface of the sheet, which is opposite the first surface, also is masked with a plurality of separated bands of photo resist, which are aligned with the bands of the first surface. However, the areas on the second surface which are to form areas of reduced thickness, such as central portion 28 and edge portion 12 (FIG. 1), thinned area 40 (FIG. 3) and thinned area 42 (FIG. 4), and the areas which are to form apertures 14, are left unmasked. Thin connecting or bridge areas between the bands may also be masked on the second surface. The sheet containing the mask is subjected to an acid etch, such as Ferric Chloride, until material is removed from the areas of reduced thickness to a desired depth. For a 0.0015 thick sheet, 0.001 inch of material may be removed to form thinned areas having a thickness of about 0.0005 inch. In addition, the acid etch completely removes material from the aligned areas of the sheet which have been left unmasked on both surfaces. This forms individual bands having open apertures 14. If connecting bridges are used, the bands are still connected together by the bridges. The mask may be removed from the individual bands, for example, in a caustic soda solution, and the bands are washed and dried.

Other techniques also may be used to produce the band. For example, apertures 14 may be formed by stamping or laser cutting. The areas of reduced thickness may be made by grinding, sandblasting, polishing, molding, casting or any other process suitable for achieving a recessed or thinned area. In another example, the area of reduced thickness (e.g., central area 28) may be made by providing an aperture entirely through the band, which is then covered by a second material of a reduced thickness to thereby form the area of reduced thickness.

While the present invention has been described in accordance with several embodiments, it is to be understood that substitutions and alterations may be made thereto without departing from the spirit and scope of the following claims. I claim all such modifications, which fall within the scope of the following claims.

I claim:

1. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including first and second spaced apart central portions positioned such that when the body is wrapped around the first tooth, the central portions are respectively positioned between the proximal surfaces of the first and second teeth and between the proximal surfaces of the first and third teeth; and
   an aperture formed in the second central portion and entirely surrounded by a portion of the body so as to permit at least partial interproximal contact between the first and third teeth through the aperture.

2. A tooth insert according to claim 1 wherein the aperture is sized to be longer in the side edge to side edge direction than in the gingival to occlusal edge direction.

3. A tooth insert according to claim 1 wherein the thickness of the body is reduced in an edge portion extending along the gingival edge below the aperture to facilitate insertion of the band through the intact interproximal contact.

4. A tooth insert according to claim 1 wherein the body is comprised of stainless steel and wherein the aperture is at least partially surrounded by an area having a thickness which is less than the thickness of the body.

5. A tooth insert according to claim 1 wherein the body has a reinforcing portion at least partially surrounding the aperture.

6. A tooth insert according to claim 1 wherein the aperture is generally oval in shape, with the major axis of the aperture extending lengthwise of the band.

7. A tooth insert according to claim 1 wherein the body has a projection extending in the occlusal direction above the aperture.

8. A tooth insert according to claim 1 wherein the body is aperture free in the first central portion.

9. A tooth insert according to claim 8 wherein at least a portion of a second body has a first thickness and wherein the thickness of at least a portion of the first central region is less than the first thickness.

10. A tooth insert according to claim 9 wherein there is only one aperture in the first and second central portions.

11. A tooth insert according to claim 10 wherein the at least a portion of the first central portion which is less than the first thickness is comprised of stainless steel.

12. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including fast and second spaced apart central portions positioned such that when the body is wrapped around the first tooth, the central portions are respectively positioned between the proximal surfaces of the first and second teeth and between the proximal surfaces of the first and third teeth;
   an aperture formed in the second central portion to permit at least partial interproximal contact between the first and third teeth through the aperture; and
   wherein the body has a reinforcing portion at least partially surrounding the aperture.

13. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including first and second spaced apart central portions positioned such that when the body is wrapped around the first tooth, the central portions are respectively positioned between the proximal surfaces of the first and second teeth and between the proximal surfaces of the first and third teeth;
   an aperture formed in the second central portion so as to permit at least partial interproximal contact between the first and third teeth through the aperture; and
   wherein the aperture is generally oval in shape, with the major axis of the aperture extending lengthwise of the band.

14. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including first and second spaced apart central portions positioned such that when the body is wrapped around the first tooth, the central portions are respectively positioned between the proximal surfaces of the first and second teeth and between the proximal surfaces of the first and third teeth;
   an aperture formed in the second central portion so as to permit at least partial interproximal contact between the first and third teeth through the aperture; and
   wherein the body has a projection extending in the occlusal direction above the aperture.

15. A tooth insert according to claim 14 wherein the projection is generally rectangular.

16. A tooth insert according to claim 14 wherein the projection is generally trapezoidal.

17. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges, the body having a thickness
   the body including first and second spaced apart central portions positioned such that when the body is wrapped around the first tooth, the central portions are respectively positioned between the proximal surfaces of the first and second teeth and between the proximal surfaces of the first and third teeth;
   an aperture formed in the second central portion so as to permit at least partial interproximal contact between the first and third teeth through the aperture;
   wherein the thickness of the body is reduced in an edge portion extending along the gingival edge below the aperture to facilitate insertion of the band through the intact interproximal contact; and
   wherein the edge portion is about 0.5 millimeter wide and about 10 to 20 millimeters long.

18. A tooth insert for insertion between the proximal surfaces of a first tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including first and second spaced apart central portions positioned such that when the body is wrapped around the first tooth, the central portions are respectively positioned between the proximal surfaces of the first and second teeth and between the proximal surfaces of the first and third teeth;
   an aperture formed in the second central portion to permit at least partial interproximal contact between the first and third teeth through the aperture; and
   wherein the body has a first thickness and the first central portion is aperture free and has a thickness which is less than the first thickness.

19. A tooth insert for insertion between the proximal surfaces of a fist tooth and a second adjacent tooth and between the first tooth and a third tooth at the opposite side of the first tooth from the second tooth, the first and third teeth forming an intact interproximal contact, the tooth insert comprising:
   a body having opposing gingival and occlusal edges and opposing side edges;
   the body including first and second spaced apart central portions positioned such that when the body is wrapped around the first tooth, the central portions are respectively positioned between the proximal surfaces of the fist and second teeth and between the proximal surfaces of the first and third teeth; and
   an aperture formed in the second central portion so as to permit at least partial interproximal contact between the first and third teeth through the aperture; and
   wherein the body has a first thickness and the aperture is entirely surrounded by an area having a thickness which is less than the first thickness of the body.

20. A tooth insert for engaging around a first tooth having a prepared proximal surface requiring restoration adjacent to a second tooth and an intact proximal surface adjacent to a third tooth at the opposite side of the first tooth from the second tooth, the tooth insert comprising:
   an elongate body having first and second leg portions such that when the insert is wrapped around the first tooth, a portion of the first leg portion is positioned between the proximal surfaces of the first and second teeth and a portion of the second leg portion is positioned between the proximal surfaces of the first and third teeth;
   an aperture formed in the second leg portion to minimize separation between the third tooth and the intact proximal surface of the first tooth when the insert is wrapped around the first tooth; and
   wherein at least a portion of the first leg portion positioned between the prepared surface of the first tooth and the third tooth when the insert is wrapped around the first tooth has no aperture and is of a reduced thickness, relative to the thickness of the body.

21. A tooth insert according to claim 20 wherein the aperture is generally oval in shape and is elongated in the side-to-side direction.

22. A tooth insert according to claim 20 wherein the aperture is dimensioned to permit full interproximal contact between the first and third teeth when the insert is positioned around the first tooth and wherein at least a portion of the second leg portion positioned between the first tooth and the second tooth is of a reduced thickness.

23. A tooth insert according to claim 20 wherein the body has a gingival edge and the second leg portion has an area of reduced thickness extending along the gingival edge under the aperture.

24. A tooth insert according to claim 20 wherein the body has an occlusal edge and the second leg portion has a projection extending in the occlusal direction.

25. A tooth insert according to claim 20 wherein the at least a portion of the first leg portion of reduced thickness is comprised of stainless steel.

26. A tooth insert for engaging around a first tooth having a prepared proximal surface requiring restoration adjacent to a second tooth and an intact proximal surface adjacent to a third tooth at the opposite side of the first tooth from the second tooth, the tooth insert comprising:

an elongate body having first and second leg portions such that when the insert is wrapped around the first tooth, a portion of the first leg portion is positioned between the proximal surfaces of the first and second teeth and a portion of the second leg portion is positioned between the proximal surfaces of the first and third teeth;

an aperture formed in the second leg portion to minimize separation between the third tooth and the intact proximal surface of the first tooth when the insert is wrapped around the first tooth; and wherein the body has an occlusal edge and the second leg portion has a projection extending in the occlusal direction.

27. A tooth insert according to claim 26 wherein the projection is generally rectangular.

28. A tooth insert according to claim 26 wherein the projection is generally trapezoidal.

29. A tooth insert for engaging around a first tooth having a prepared proximal surface requiring restoration adjacent to a second tooth and an intact proximal surface adjacent to a third tooth at the opposite side of the first tooth from the second tooth, the tooth insert comprising:

an elongate body having first and second leg portions such that when the insert is wrapped around the first tooth, a portion of the first leg portion is positioned between the proximal surfaces of the first and second teeth and a portion of the second leg portion is positioned between the proximal surfaces of the first and third teeth;

an aperture formed in the second leg portion to minimize separation between the third tooth and the intact proximal surface of the first tooth when the insert is wrapped around the first tooth; and wherein the aperture is at least partially surrounded by a first area having a first thickness and a reinforcing portion surrounding the first area and having a second thickness greater than the first thickness.

30. A method of restoring a tooth which has two proximal surfaces, the fist of which is an intact surface and the second of which is a prepared surface having a cavity, the method comprising:

positioning an elongated band around the tooth such that a first central portion of the band is positioned adjacent to the intact proximal surface of the tooth and a second central portion spaced from the first central portion is positioned adjacent to the prepared proximal surface of the tooth, the first central portion having an entirely surrounded aperture, the aperture minimizing separation between the intact proximal surface and an adjacent tooth, and the second central portion being aperture free to retain filling material introduced into the cavity, and introducing filling material into the cavity.

31. The method according to claim 30 wherein the first central portion has an area of reduced thickness below the aperture, the area of reduced thickness being of a first thickness and the first central portion having at least one area of a second thickness, the first thickness being less than the second thickness.

32. A tooth insert according to claim 30 wherein the band extends in the occlusal direction to form a projection above the aperture.

33. A method of restoring a tooth which has two proximal surfaces, the first of which is an intact surface and the second of which is a prepared surface having a cavity, the method comprising:

positioning an elongated band around the tooth such that a first central portion of the band is positioned adjacent to the intact proximal surface of the tooth and a second central portion spaced from the first central portion is positioned adjacent to the prepared proximal surface of the tooth, the first central portion having an aperture to minimize separation between the intact proximal surface and an adjacent tooth;

introducing filling material into the cavity; and wherein the band extends in the occlusal direction to form a projection above the aperture.

34. A tooth insert for restoring a tooth which has two proximal surfaces, the first of which is an intact surface and the second of which is a prepared surface having a cavity, the insert comprising:

containing means for containing filing material introduced into the cavity when positioned around the tooth, said containing means extending across the intact surface and the prepared surface;

enclosed aperture means for minimizing separation between the intact surface and an adjacent tooth when said containing means is positioned around the tooth to be restored;

wherein the containing means comprises an elongated band the band, having at least a portion of a first thickness; and wherein the means for minimizing separation between the intact surface and an adjacent tooth comprises an enclosed aperture formed in a portion of the band and positioned adjacent the intact surface when the band is positioned around the tooth to be restored, the aperture being bounded at least in part by the portion of the band of a second thickness, which is less than the first thickness.

35. A tooth insert for wrapping substantially around a first tooth having a prepared proximal surface requiring restoration adjacent to a second tooth and an intact proximal surface adjacent to a third tooth at the opposite side of the fist tooth from the second tooth, the tooth insert comprising:

an elongate body having opposite gingival and occlusal edges and opposite side edges extending between the gingival and occlusal edges, the body having first and second leg portions such that when the insert is wrapped around the first tooth, a portion of the first leg portion is positioned between the proximal surfaces of the first and second teeth and a portion of the second leg portion is positioned between the proximal surfaces of the first and third teeth;

an aperture formed in the second leg portion to minimize separation between the third tooth and the intact proximal surface of the first tooth when the insert is wrapped around the first tooth; and the second leg portion having a projection above the aperture extending in the occlusal direction and an area of reduced thickness extending along the gingival edge under the aperture to facilitate insertion of the second leg portion between the first and third teeth.

* * * * *

UNITED STATES PATENT AND TRADEMARK OFFICE
CERTIFICATE OF CORRECTION

PATENT NO.    : 6,736,639 B1
DATED         : May 18, 2004
INVENTOR(S)   : John D. Summer It is certified that error appears in the above-identified patent and that said Letters Patent is hereby corrected as shown below:

Column 8,
Lines 41-42, "portion of a second body has a first thickness and wherein the thickness of at least" should read -- portion of the body has a first thickness and wherein a second thickness of at least --

Column 10,
Lines 22 and 33, "fist" should read -- first --

Column 11,
Line 60, "fist" should read -- first --

Column 13,
Line 37, "filing" should read -- filling --
Line 61, "fist" should read -- first --

Signed and Sealed this

Twenty-first Day of June, 2005

JON W. DUDAS
*Director of the United States Patent and Trademark Office*